United States Patent [19]

Wallner et al.

[11] Patent Number: 5,298,489

[45] Date of Patent: Mar. 29, 1994

[54] DNA SEQUENCES RECOMBINANT DNA MOLECULES AND PROCESSES FOR PRODUCING LIPOCORTINS III, IV, V AND VI

[75] Inventors: Barbara P. Wallner, Cambridge; R. Blake Pepinsky, Watertown; Jeffrey L. Browning, Cambridge, all of Mass.

[73] Assignee: Biogen, Inc., Cambridge, Mass.

[21] Appl. No.: 668,744

[22] Filed: Mar. 13, 1991

Related U.S. Application Data

[63] Continuation of Ser. No. 160,866, Feb. 26, 1988.

[51] Int. Cl.$^5$ .................. C07K 13/00; C12N 15/12
[52] U.S. Cl. ................................ 514/12; 530/350; 435/69.1; 435/320.1; 536/23.5
[58] Field of Search .................. 530/350, 395; 514/12; 435/69.2, 69.1, 320.1; 536/27, 23.5

[56] References Cited

U.S. PATENT DOCUMENTS

| | | | |
|---|---|---|---|
| 4,239,780 | 12/1980 | Wallach | 424/330 |
| 4,332,892 | 6/1982 | Ptashe et al. | 435/68 |
| 4,338,397 | 7/1982 | Gilbert et al. | 435/68 |
| 4,425,437 | 1/1984 | Riggs | 435/317 |
| 4,530,901 | 7/1985 | Weissmann | 435/70 |
| 4,537,858 | 8/1985 | O'Sullivan et al. | 435/119 |
| 4,874,743 | 10/1989 | Wallner | 514/12 |
| 4,937,324 | 6/1990 | Fujikawa | 530/397 |

FOREIGN PATENT DOCUMENTS

WO8606100 10/1986 World Intellectual Prop .
WO8805659 11/1988 World Intellectual Prop .
WO8807576 10/1988 World Intellectual Prop .

OTHER PUBLICATIONS

E. Amann et al., "Vectors Bearing a Hybrid trp lac Promoter Useful For Regulated Expression of Cloned Genes in *Escherichia coli*", *Gene*, 25, pp. 167-178 (1983).
G. J. Blackwell et al., "Glucocorticoids Induce The Formation And Release of Anti-Inflammatory and Anti-Phospholipase Proteins into the Peritoneal Cavity Of The Rat", *Br. J. Pharmac.*, 76, pp. 185-194 (1982).
K. Biemann and H. A. Scoble, "Characterization By Tandem Mass Spectrometry of Structural Modifications In Proteins", 237, pp. 992-998 (1987).
J. S. Brugge, "The p35/p36 substrates of Protein-tyrosine Kinases As Inhibitors of Phosphilipase A$_2$", *Cell*, 46, pp. 149-150 (1986).
J. Chirgwin et al., "Isolation of Biologically Active Ribonucleic Acid From Sources Enriched In Ribonuclease", *Biochemistry*, 18, pp. 5294-5299 (1979).
G. Church and W. Gilbert, "Genomic Sequencing" *Proc. Nat. Acad. Sci. U.S.A.*, 81, pp. 1991-1995 (1984).
G. Cirino and R. J. Flower, "Human Recombinant Lipocortin I Inhibits Prostacyclin Production By Human Umbilical Artery *In Vitro*", *Prostaglandins*, 34, pp. 59-62 (1987).
G. Cirino et al., "Recombinant Human Lipocortin I Inhibits Thromboxane Release From Guinea-Pig Isolated Perfused Lung", *Nature*, 328, pp. 270-272 (1987).
J. F. Cloix et al., "Characterization And Partial Purification of 'Renocortins': Two Polypeptides Formed in Renal Cells Causing The Anti-Phospholipase-Like Action of Glucocorticoids", *Br. J. Pharmac.*, 79, pp. 313-321 (1983).
C. E. Creutz et al., "Characterization Of The Chromobindins: Soluble Proteins That Bind to The Chromaffin Granule Membrane In The Presence of Ca$^{2+}$", *J. Biol. Chem.*, 258, pp. 14664-14674 (1983).

(List continued on next page.)

Primary Examiner—Robert J. Hill, Jr.
Assistant Examiner—John D. Ulm
Attorney, Agent, or Firm—James F. Haley, Jr.; David J. Meyer; Gary L. Creason

[57] ABSTRACT

Human lipocortins III, IV, V and VI, DNA sequences and recombinant DNA molecules that are characterized in that they code for these human lipocortins. Hosts transformed with these sequences may be employed in the processes of this invention to produce the human lipocortin molecules of this invention. These polypeptides possess anti-inflammatory activity and are useful in the treatment of arthritic, allergic, dermatologic, ophthalmic and collagen diseases.

5 Claims, 6 Drawing Sheets

OTHER PUBLICATIONS

C. E. Creutz et al., "Identification of Chromaffin Granule-Binding Proteins", *J. Biol. Chem.*, 262, pp. 1860–1868 (1987).

M. R. Crompton et al., "Primary Structure Of The Human, Membrane-Associated $Ca^{2+}$-binding Protein p68: A Novel Member Of A Protein Family", *EMBO J.*, 7, pp. 21–27 (1988).

F. F. Davidson et al. "Inhibition Of Phospholipase $A_2$ By 'Lipocortins' and 'Calpactins'", *J. Biol. Chem.*, 262, pp. 1698–1705 (1987).

A. D. Davies and M. J. Crumpton, "Identification Of Calcium-Binding Proteins Associated With The Lymphocyte Plasma Membrane", *Biochem. and Biophys. Res. Comm.*, 128, pp. 571–577 (1985).

B. K. De et al., "A Calcium-Dependent 35-Kilodalton Substrate for Epidermal Growth Factor Receptor/Kinase Isolated From Normal Tissue", *J. Biol. Chem.*, 261, pp. 1374–1392 (1986).

R. Devos et al., "Molecular Cloning Of Human Interleukin 2 cDNA And Expression in *E. coli*", *Nucleic Acids Research*, 11, 4307–23 (1983).

P. Dimond, "Biogen Produces Recombinant Anti-Inflammatory Agent", *Genetic Engineering News*, 5, p. 12 (1985).

M. DiRosa et al., "Anti-Phospholipase Proteins", *Prostaglandins*, 28, pp. 441–442 (1984).

E. Erikson et al., "Identification Of A Cellular Protein Substrate Phosphorylated By the Avian Sarcoma Virus Transforming Gene Product", *Cell*, 21, pp. 829–836 (1980).

E. Erikson et al., "Biochemical Characterization Of a 34 Kilodalton Normal Cellular Substrate of $pp60^{v-arc}$ And An Associated 6-Kilodalton Protein", *Mol. Gen. Biol.*, 4, pp. 77–85 (1984).

M. Errasfa et al., "The Presence Of Lipocortin In Human Embryonic Skin Fibroblasts And Its Regulation By Anti-Inflammatory Steroids", *Biochem. et Biophys. Acta*, 847, pp. 247–254 (1985).

J. Etienne and J. Polyonovski, "Phospholipase $A_2$ Activity In Rate And Human Lymphocytes", *Biochem. and Biophys. Res. Comm.*, 125, pp. 719–727 (1984).

R. Fava and S. Cohen, "Isolation of a Calcium-Dependent 35 Kilodalton Substrate For the Epidermal Growth Factor Receptor/Kinase From A-431 Cells", *J. Biol. Chem.*, 259, pp. 2636–2645 (1984).

J. Fauvel et al. "Lipocortin-like Anti Phospholipase $A_2$ Activity of Endonexin", *FEBS Letts.*, 216, pp. 45–50 (1987).

R. J. Flower and G. J. Blackwell, "Anti-Inflammatory Steroids Induce Biosynthesis Of A Phospholipase $A_2$ Inhibitor Which Prevents Prostaglandin Generation", *Nature*, 278, pp. 456–459 (1979).

R. J. Flower et al., "Macrocortin and the Mechanism of Action of the Glucocoirticoids", *Adv. in Inflm. Res.*, 7, pp. 61–70 (1984).

T. Funakoshi et al., "Human Placental Anticoagulant Protein: Isolation and Characterization", *Biochemistry*, 26, pp. 5572–5578 (1987).

T. Funakoshi et al. "Primary Structure Of Human Placental Anticoagulant Protein", *Biochemistry*, 26, pp. 8087–8092.

M. J. Geisow, "Common Domain Structure of $Ca^{2+}$ And Lipid-Binding Proteins", *FEBS Letts.*, 204, pp. 99–103 (1986).

M. J. Geisow et al. "A Consensus Amino Acid Sequence Repeat in *Torpedo* And Mammalian $Ca^{2+}$—dependent Membrane-Binding Proteins", *Nature*, 320, pp. 636–638 (1986).

V. Gerke and K. Weber, "Identity of p36K Phosphorylated Upon Rous Sarcoma Virus Transformation with a Protein Purified from Brush Borders; Calcium—Dependent Binding to Non-Erythroid Spectrin and F-Actin", *EMBO Journal*, 3, pp. 227–233 (1984).

V. Gerke and K. Weber, "Calcium-Dependnet Conformational Changes in the 36-kDa Subunit of Intestinal Protein I Related To the Cellular 36-kDa Target of Rous Sarcoma Virus Tyrosine Kinase", *J. Biol. Chem.*, 260, pp. 1988–1995 (1985).

J. Glenney and B. F. Tack, "Amino-Terminal Sequence of p36 And Associated p10: Identification Of The Site of Tyrosine Phosphorylation And Homology With S-100", *Proc. Nat. Acad. Sci U.S.A.*, 82, pp. 7884–7888 (1985).

J. Glenney, "Two Related But Distinct Forms Of The $M_r$ 36,000 Tyrosine Kinase Substrate (Calpactin) That Interact With Phospholipid and Actin In A $Ca^{2+}$ Dependent Manner", *Proc. Nat. Acad. Sci. U.S.A.*, 84, pp. 4258–4262 (1986).

U. Grundmann et al. "Characteriztion Of cDNA Encoding Human Placental Anticoagulant Protein (PP4): Homology With The Lipocortin Family", *Proc. Nat. Acad. Sci. U.S.A.*, 85, pp. 3708–3712 (1988).

(List continued on next page.)

OTHER PUBLICATIONS

D. Hager and R. Burgess, "Elution Of Proteins From Sodium Dodecyl Sulfate-Polyacrylamide Gels, Removal Of Sodium Dodecyl Sulfate, And Renaturation Of Enzymatic Activity: Results With Signma Subunit of Escherichia coli RNA Polymerase, Wheat Germ DNA Topoisomerase, And Other Enzymes", *Anal. Biochem.*, 109, pp. 76, 86 (1980).

H. T. Haigler et al. "Characterization Of Lipocortin In And An Immunologically Unrelated 33-kDa Protein As Epidermal Growth Factor Receptor/Kinase Substrates And Phospholipase $A_2$ Inhibitors", *J. Biol. Chem.*, 262, pp. 6921-6930.

H. T. Haigler et al. "cDNA Sequence Of Human Endonexin II: Homology With Lipocortin, Calpactin and Protein II", *J. Cell Biochem.*, Suppl. p. 92 (abstr.) (1988).

H. C. Hamman et al. "Cloning And Characterization Of A cDNA Encoding Bovine Endonexin (Chromobindin 4)", *Biochem. and Biophys. Res. Comm.*, 156, pp. 66067 (1980).

T. Hattori et al., "Inhibition Of Human Natural Killer (NK) Activity and Antibody Dependent Cellular Cytotoxicity (ADCC) By Lipomodulin, A Phospholipase Inhibitory Protein", *J. Immunol.*, 131, pp. 262-265 (1983).

T. Hattori et al., "Inhibition Of Human Natural Killer (NK) Activity and Antibody Dependent Cellar Cytotoxicity (ADCC) By Lipomodulin, A *Phospholipase Inhibitory Protein*", *Chem. Abstr.*, 99, #86478r (1983).

F. Hirata et al., "A Phospholipase $A_2$ Inhibitory Protein In Rabbit Neutrophils Induced By Glucocorticoids", *Proc. Nat. Acad. Sci. U.S.A.*, 77, pp. 2533-2536 (1980).

F. Hirata, "The Regulation of Lipomodulin, A Phospholipase Inhibitory Protein In Rabbit Neutrophils By Phosphorylation", *J. Biol. Chem.*, 256, pp. 7730-7733 (1981).

F. Hirata et al., "Presence of Autoantibody For Phospholipase Inhibitory Protein, Liopmodulin In Patients With Rheumatic Disease", *Pro. Nat. Acad. Sci. U.S.A.*, 78, pp. 3190-3194 (1981).

F. Hirata et al., "Identification Of Several Species of Phospholipase Inhibitory Protein(s) by Radioimmunoassay For Lipomodulin", *Biochem. Biophys. Res. Commun.*, 109, pp. 223-230 (1982).

F. Hirata "Roles of Lipomodilin: A Phosphilipase Inhibitory Protein In Immunoregulation", *Adv. Inflm. Res.*, 7, pp. 71-78 (1984).

F. Hirata "Roles of Lipomodulin: A Phospholipase Inhibitory Protein In Immunoregulation", *Chem. Abstracts*, 100, #119189s (1984).

F. Hirata et al., "Inhibition of Leukocyte Chemotaxis By Glu-Glu-Glu-Glu-Tyr-Pro-Met-Glu And Leu-Ile-Glu-Asp-Asn-Glu-Tyr-Thr-Ala-Arg-Gln-Gly", *Biochem. Biophys. Res. Comm.*, 118 pp. 682-690 (1984).

F. Hirata et al, "Isolation And Characterization Of Lipocortin (Lipomodulin)", *Agents And Actions*, 17, pp. 263-266 (1985).

K. Huang et al., "Two Human 35 kd Inhibitors Of Phospholipase $A_2$ Are Related To Substrates of $pp60^{v-arc}$ And Of The Epidermal Growth Factor Receptor/Kinase", *Cell*, 46, pp. 191-199 (1986).

K. Huang et al., "Purification And Characterization Of Proteolytic Fragments Of Lipocortin I That Inhibit Phospholipase $A_2$", *J. Biol. Chem.*, 262, pp. 7639-7645 (1987).

M. Hunkapiller et al., "Isolation Of Microgram Quantities Of Proteins From Polyacrylamide Gels For Amino Acid Sequence Analysis", *Meth. In Enzym.*, 91, pp. 227-236 (1983).

D. Iserentant and W. Fiers, "Secondary Structure Of mRNA And Efficiency Of Translation Initiation", *Gene*, pp. 1-12 (1980).

A. Iwasaki et al., "Structure And Expression Of cDNA For An Inhibitor Of Blood Coagulation Isolated From Human Placenta: A New Lipocortin-Like Protein", *J. Biochem.*, 102, pp. 1261-1273 (1987).

A. Iwasaki et al. "Structure and Expression of cDNA For Calphobindin II, A Human Placental Coagulation Inhibitor", *J. Biochem.*, 106, pp. 43-49, (1989).

N. Johnsson et al., "Binding Sites For Calcium, Lipid And p11 on p36, The Substrate Of Retroviral Tyrosine-specific Protein Kinases", *FEBS Letts*, 198, pp. 361-364 (1986) (Johnsson et al., (1986a)).

N. Johnsson et al., "Functionally Distinct Serine Phosphorylation Sites of p36, The Cellular Substrate Of Retroviral Protein Kinase; Differential Inhibition Of Reassociation With p11", *EMBO J.*, 5, pp. 3455-3460 (1986).

M. A. Kaetzel et al. "Differential Tissue Expression Of Three 35-kDa Annexin Calcium-dependent Phospholipid Binding Proteins", *J. Biol. Chem.*, 264, pp. 14463-14470 (1989).

(List continued on next page.)

OTHER PUBLICATIONS

R. Kaplan et al. "Cloning And Expression of cDNA for Human Endonexin II, A $Ca^{2+}$ and Phospholipid Binding Protein", *J. Biol. Chem.*, 263, pp. 8037–8043 (1988).

R. H. Kretsinger and C. E. Creutz., "Consensus In Exocytosis", *Nature*, 320, p. 573 (1986).

R. Lawn et al., "The Isolation And Characterization Of Linked delta And β-Globin Genes From A Cloned Library of Human DNA", *Cell*, 15, pp. 1157–1174 (1978).

H. Lehrach et al., "RNA Molecular Weight Determinations By Gel Electrophoresis Under Denaturing Conditions, A Critical Reexamination", *Biochemistry*, 16, pp. 4743–4751 (1977).

I. Mancheva et al., "The Primary Structure Of The Inhibitor of Vipoxin From The Venom Of The Bulgarian Viper (Vipera ammodytes *ammodytes Serpentes*)", Hoppe-Selve's Z. Physiol. Chem., 365, pp. 885–894 (1984).

I. Mancheva et al., "Sequence Homology Between Phospholipase And Its Inhibitor In Snake Venom: The Primary Structure Of The Inhibitor Of Vipoxin From The Venom Of The Bulgarian Viper", *Biol. Abstr*, 79, #39874 (1984).

T. Maniatis et al., *Molecular Cloning (A Laboratory Manual)*, pp. 5–6, 405–414 (1984).

G. J. Blackwell et al., "Macrocortin: A Polypeptide Causing The Anti-Phospholipase Effect of Glucocorticoids", *Nature*, 287, pp. 147–149 (1980).

A. Maxam and W. Gilbert, "A New Method For Sequencing DNA", *Proc. Nat. Acad. Sci. U.S.A.*, 74, pp. 560–564 (1977).

Rothhut, B. et al. "Purification and Characterization of a 32kDa Phospholipase A2 inhibitory . . . " FEBS Letters vol. 219(1) 169–175 (Jul. 1987).

Tai, J. F. et al. "Placental Anticoagulant Proteins . . . " Biochemistry 27(17) pp. 6268–6276 (1988, not prior art).

N. G. Ahn et al. "Sedimentation Equilibrium Analysis Of Five Lipocortin-related Phospholipase A2 Inhibitors From Human Placenta", *J. Biol. Chem.*, 263, pp. 18657–18663 (1988).

Y. Morinaga et al., "Improvement of Oligonucleotide-Directed Site-Specific Mutagenesis Using Double Stranded Plasmid DNA", *Biotechnology*, 2, pp. 636–639 (1984).

J. F. Morrow, "Recombinant DNA Techniques", *Methods In Enzymology*, 68, pp. 3–24 (1979).

R. Mulligan and P. Berg, "Selection For Animal Cells That Express The *Escherichia coli* Gene Coding For Xanthine–Guanine Phosphoribosyltransferase", Proc. Nat. Acad. Sci. U.S.A., 78, pp. 2072–2076 (1981).

N. Murray et al., "Molecular Cloning of DNA Ligase Gene From Bacteriophage T4 II. Amplification And Preparation Of Gene Product", *J. Mo. Biol.*, 132, pp. 493–505 (1979).

N. Murray et al., "Lambdoid Phages That Simplify The Recovery Of In Vitro Recombinants", *Mol. Gen. Genetics*, 150, pp. 53–61 (1977).

Nelson, M. R. et al., "Expression Of Endonexin In Escherichia Coli Using Site Directed Mutagnesis", *J. Cell Biol.*, 107, p. 340A (1988).

Oroszlan, et al., "Amino–And Carboxyl–Terminal Amino Acid Sequences Of Proteins Coded By gag Gene Of Murine Leukemia Virus", *Proc. Nat. Acad. Sci. U.S.A.*, 75, pp. 1404–1408 (1977).

R. Owens and M. Crumpton, "Isolation and Characterization of a Novel $68,000-M_r$ $Ca^{+2}$-binding Protein Of Lymphocyte Plasma Membrane.", *Biochem J.*, 219, pp. 309–316 (1984).

R. B. Pepinsky, "Localization Of Lipid–Protein And Protein–Protein Interactions Within The Murine Retrovirus gag Precursor By A Novel Peptide-mapping Technique", J. Biol. Chem. 258, pp. 11229–11235 (1983).

R. B. Pepinsky et al., "Purification And Partial Sequence Analysis of a 37-kDa Protein That Inhibits Phospholipase A2 Activity From Rat Peritoneal Exudates", *J. Biol. Chem.*, 261, pp. 4239–4246 (1986).

R. B. Pepinsky and L. J. Sinclair, "Epidermal Growth Factor-Dependent Phosphorylation Of Lipocortin", *Nature*, 321, pp. 81–84 (1986).

R. B. Pepinsky et al., "Five Distinct Calcium And Phospholipid Binding Proteins Share Homology With Lipocortin I", *J. Biol. Chem.*, 262, pp. 10799–10811 (1988).

K. Radke et al., "Transformation By Rous Sarcoma Virus: A Cellular Substrate For Transformation-Specific Protein Phosphorylation Contains Phosphotyrosine", Cell, 21, pp. 821–828 (1980).

B. Rothhut et al., "Further Characteriztion Of The Glucocorticoid-Induced Antiphospholipase Protein 'Renocortin'", *Biochem. Biophys. Res. Commun.*, 117, pp. 878–884 (1983).

(List continued on next page.)

```
  1 GAATTCCGATTAGTGTGATCTCAGCTCAAGGCAAAGTGTGGGATATCATGGCATCTATCTGGTTGGACACCGAGGAACAGTAAGAGATTATCCAGACTTT
                                      MetAlaSerIleTrpValGlyThrValArgGlyHisArgValThrProLysArgAspTyrProAspPhe                    100

101 AGCCCATCAGTGATGCTGAAGCTATTCAGAAAGCAATTCAGAGGAATTGAACTGATGAGAAATTGCTCATCAGATTCTGACTGAGAGGTCAAATGCAC
    SerProSerValAspAlaGluAlaIleGlnLysAlaIleGlnArgGlyIleArgAspMetArgAsnSerSerSerIleLeuThrGluArgSerAsnAlaG           200

201 AGCGGCAGCTGATTGTTAAGGAATATCAAGCAGCATATGGAAAGATGAAAGCTGAAAGTCTGGCCACTTTGAGCATCTCATGT
    lnArgGlnLeuIleValLysGluValTyrGlnAlaAlaTyrGlyIleValLysGluLeuLysAspLeuLysGlyAspLeuSerGlyHisLeuHisMetVa           300

301 GGGCCCTAGTGACTCCACCAGTCTTTGATGCAAAGCAGTCTAAAGAATCATGAAGGCGGAACAAAGAAGATGCCTTGATGAAATCTTAACT
    lAlaLeuValThrProProAlaValPheAspAlaLysGlnSerLysMetLysSerMetLysGlyAlaGlyThrAsnGluAspAlaLeuIleLeuLeuThr              400

401 ACCAGGACAAGCAGGCAAATGAAAGATATCTCTCAAGCTATTACAGAAGAGTCTTGAGATGACATTAGTTCCGAAACATCTGTGACT
    ThrArgThrSerArgGlnMetLysAspIleSerGlnAlaTyrTyrThrValTyrLysLysValGlyAspIleSerSerGluThrSerGlyAspP              500

501 TCCGAAAGTCTCTGTTGACTTTGGCAGATGGCAGAAGATCTGAAGTCTGCAAGAGATCTCGCCAAACAGATGCCCAGATTCTCTATAAAGC
    heArgLysAlaLeuLeuThrLeuAlaLeuLeuHisLeuAlaLysAlaGlnIleLeuTyrLysAl                                               600

601 TGGTGAGAACAGATGGGCAGGACATTGTGACAGCTGAAGACAAATTCACTGAAGACTTCAATTAAACATTTGATGAATACAGAAT
    aGlyGluAsnArgTrpGlyThrAspAspAspGluIleLeuArgSerPheThrGluLysLeuThrPheAspGluTyrArgAsn                              700

701 ATCAGCCAAAGACATTGTGACACAGCATAAAGGAGAATTATCTGGGCATTTGAAGACTTACTGTGTGAGGAACACGCCGG
    IleSerGlnLysIleValAspSerIleLysGlyGluLeuGlyHisPheGluAspLeuLeuAlaIleValAlaAsnCysValArgAsnThrProA                  800

801 CCTTTTTAGCCCAAAGACTGCATCGAGCTTGAAGGTACTTACTCTGAACTGAGTTACTCCAGATCAGAAATTGACCTTTT
    laPheLeuAlaGluLeuHisArgLeuHisLysGlyIleGlyThrAspPheLeuAsnArgIleMetValSerArgSerGluIleAspLeuLe                    900

901 GGACATTGCAACAGAGTTCAAGAAGCAGTTCAAGGACATTATGGCTATTCCCTATATTGGAGACTATCTGAACATAAATGGATACACTCTTAAAATC
    uAspIleArgThrGluPheLysLysGlnPheLysAspIleMetAlaIleProTyrLeuTyrSerAspThrSerGlyAspThrLeuLeuLysIle                 1000

1001 TGTGGTGAGATGACTGAACCAAGAAGATAATCTCCAAAGGTCTCCAACAGCTCCACCTACTCTCTTCTCATACTATTTAAGAGAAC
     CysGlyGluMetThrGluProArgArgIleSerProSerTyrSerLeuTyrSerLeuTyrSerAspThrSerGluIleThrLeuLeuLysIle                  1100

1101 AAGCAAATATAAACAGCAACTGTCTTCCTAACAGGAATTTCATTGTTCTATAACAACAAAAGGATTATTTATTTAGAGCATCTCATTATA                      1200

1201 ATGTAGCAGCTCATAAATGAAATGTATTAAAGATCTGCAACTACTATCCAACTACTATATTTCTGCTTTCAAAGTTAAGAATCTTTATAGTTCT            1300

1301 ACTCCATTAAATATAAAGCAAGATAATAAAACGGAATTC    1339
```

FIG. 3

```
   1  GCGGGCCGGATCCTTCAGCGCTCTGATCTCGGCGTCGCCCCGGCCGTCGCCCCGGGCGTCTCCCCCGGGGTTCGGGCACTTGGTCCCAC                                                                                    100

101  AGTCTGGTCCTGCTTCACCTTCCCCTGACCTGAGTAGTCGCCATGGCAGCCACTGTCCTGAGTTGATTGAGCGGGCTG                                                                                                200
                                      MetAlaGlnValLeuArgGlyThrValThrAspPheProGlyPheAspGluArgAlaA

201  ATGCAGAAACTCTTCGAAGGCTATGAAAAGGCTTGGGCACAGATGAGGAGCATCTGACTCTGTTGACATCCCGAAGTAATGCTCAGCGCCAGGAAAT                                                                             300
      spAlaGlnThrLeuPheLeuArgLysAlaMetLysGlyLeuGlyThrAspGluGluSerIleLeuThrLeuLeuThrSerArgSerAsnAlaGlnArgGlnGluIl

301  CTCTGCAGCTTTAAGACTCTGTTGCAGGGATCTCTGATGACCTGAAATCAGAACTAACTGAAACTGAAAAATTAATTGTGGCTCTGATGAA                                                                                   400
      eSerAlaAlaPheLysThrLeuPheGlyArgAspLeuLeuAspAspLeuLysSerGluLeuThrGlyLysPheGluLysLeuIleValAlaLeuMetLys

401  CCCTCTCGGCTTTATGATGCTTATGAAACATGCTTGAAGGAGCTGAACAAATGAAAAAGTACTGACAGAAATTATTGCTTCAAGGACACCTG                                                                                   500
      ProSerArgLeuTyrAspAlaTyrGluLysHisAlaLeuLysLysHisAlaLeuLysThrAsnGluLysValLeuThrGluIleIleAlaSerArgThrProG

501  AAGAACTGAGAGCCATCAAACAAGTTATGAAGAAGAAATATGCTCAAGCCTGAAGGCTGAAGATGACGTGGGGGACACTTCAGGTACTACCAGCCAGGATGTT                                                                       600
      luGluLeuArgAlaIleLysGlnValTyrGluGluGluTyrGlyLysSerLeuGluSerLeuGluAspAspValValGlyAspThrSerGlyTyrTyrGlnArgMetLe

601  GCTGGTTCTCCTGAGGCTATGCTGAATTGATGAAGCTCAAGTTGAACAAGATGCTCAGCCTTTATTTCAGGCTGAGAACTTAAA                                                                                           700
      uValValLeuLeuGlnAlaAsnArgAspProAlaGlyIleLeuPheAspAlaGlnAlaGluProPheGlnAlaGlyLeuPheGlnAlaGlyGluLeuLys

701  TGGGGACAGATGAAGAAAAGTTTATCACCATCTTTGAACACGAAGTGTCTCATTGAGAAAGTGTTTGACAAGTACTATATCAGGATTTC                                                                                      800
      TrpGlyThrAspGluGluLysPheIleThrIlePheGlyThrArgSerValSerHisLeuArgSerLeuValPheAspLysTyrMetThrIleSerGlyPheG

801  AAATTGAGGAAACCATTGACCCGGAGACTTCTGCCAATTAGAGACTAACTCTATTCGAAATCTATTCGAAGTATACCTGCCTACCTTGCAGA                                                                                   900
      lnIleGluGluThrIleAspProGluThrSerAlaAsnLeuGlnLeuLeuAsnLeuLeuAlaValValLysSerIleArgSerIleProAlaTyrLeuAlaGl

901  CACCCTCTATTATGCTATGAAGGAGCTGGACAGAGTCTGGACAGATGATCATACCCTCATCAGAGTTCCAGAGTCATGTTGATCTGTTAACATCAGAAG                                                                            1000
      uThrLeuTyrTyrAlaMetLysGlyAlaGlyThrAspAspHisThrLeuIleArgValMetValSerArgSerGluIleAspLeuPheAsnIleArgLys

1001  GAGTTTAGGAAGAATTTTGCCACCTCTCTTATTCCATGATTAAGGGAGATACATCTGGGACTATAAGAAAGCTCTCTGTGGAAGATG                                                                                        1100
      GluPheArgLysAsnPheAlaThrSerLeuTyrSerMetIleLysGlyAspThrSerGlyLeuLysLysLeuLeuLeuLeuCysGlyGluAspA

1101  ACTAAGGTGTCACGGGGAAGAGCTCCCTGCTGTGCCTGCACCACCCCACTGCCTTCAGCACCTTTAGCTGCTCTTGTATGCCAGTGCTTAACAC                                                                                 1200
      sp

1201  ATTGCCTATTCATACTAGCATGCTCATGACCAACACATACACGTCATAGAAGAAATAGTGTGCTTCTTCTGATCTCTAGTGAGATCTCTTTGACT                                                                                1300

1301  GCTGTAGTACTAAAGTGTACTTAATGTTACTAAGTTAATGCTCGGCCATTTTCCATTTATATATATATTTTAAGAGGCTAGAGTGCTTTTAGCCTTTT                                                                             1400

1401  TTAAAACTCCATTTATATTACATTGTAACCATGATACATTTAATCAGAAGCTTAGCCTGAAATTGTGAACTCTTGAAATGTTATTAGTGAAGTTCGC                                                                               1500

1501  AACTAAACTAACCTGTAAAATTATGATGATTGTATTCAAAAGATTAATGAAAAATAAACATTTCTGCGGCCGC 1574
```

FIG. 4

FIG. 7
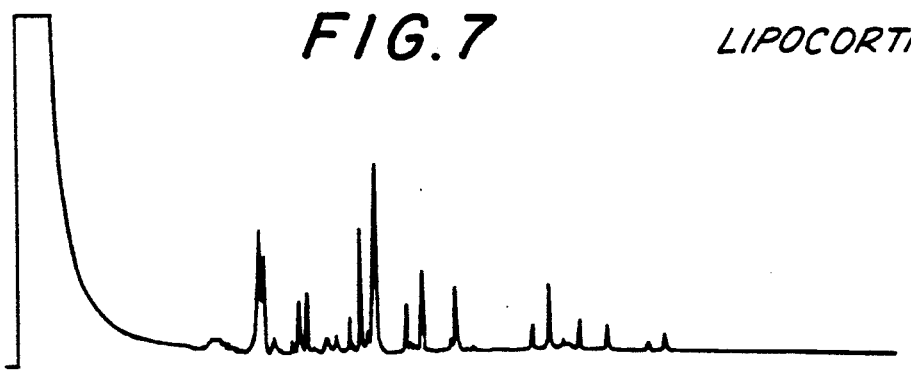
LIPOCORTIN-II
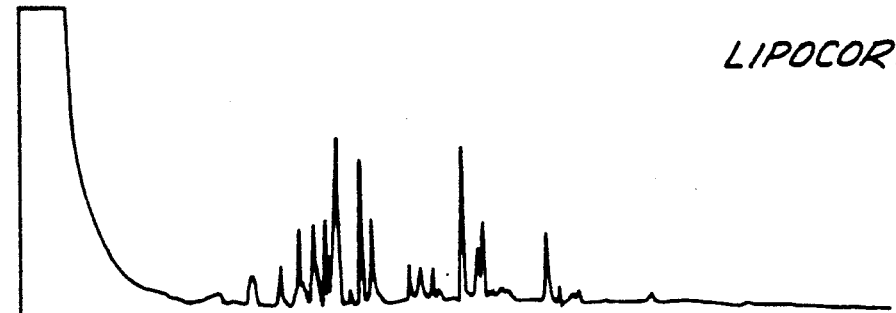
LIPOCORTIN-III
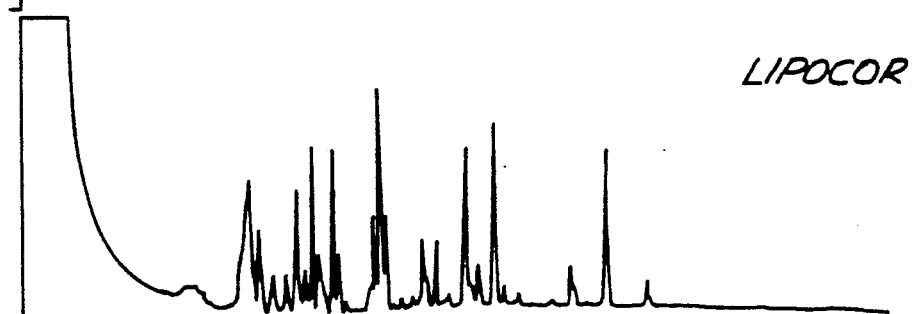
LIPOCORTIN-IV
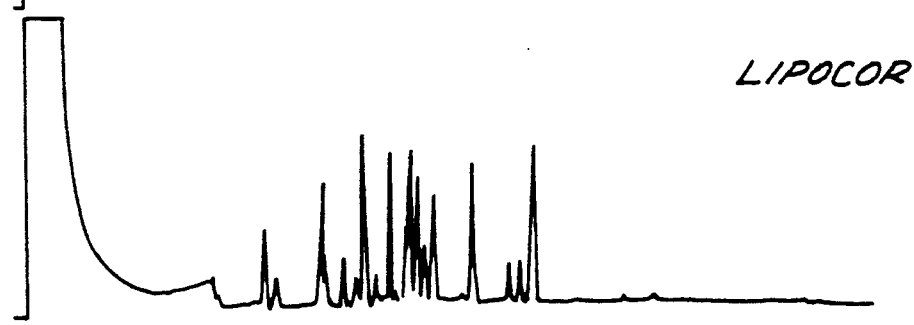
LIPOCORTIN-V
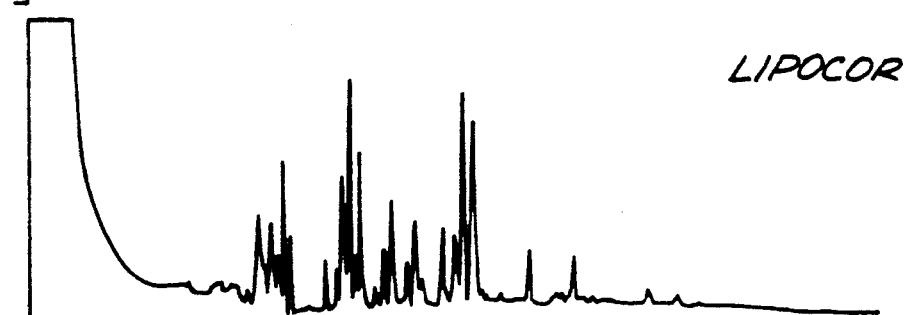
LIPOCORTIN-VI
0  10  20  30  40  50  60  70  80  90  100  110  120  130  140  150  160  170
fraction number

DNA SEQUENCES RECOMBINANT DNA MOLECULES AND PROCESSES FOR PRODUCING LIPOCORTINS III, IV, V AND VI

This is a continuation of application Ser. No. 160,866, filed Feb. 26, 1988, entitled DNA Sequences, Recombinant DNA Molecules and Processes for Producing Lipocortins III, IV, V and VI, now abandoned.

BACKGROUND OF THE INVENTION

Lipocortins are a family of proteins that have been implicated in the regulation of various aspects of inflammation [R. J. Flower et al., "Macrocortin And The Mechanism Of Action Of The Glucocorticoids", *Advances in Inflammation Research*, 7, pp. 61–9 (1984); M. DiRosa, "Role In Inflammation Of Glucocorticoid-Induced Phospholipase Inhibitory Proteins", *Prog. Biochem. Pharmacol.*, 20, pp. 55–62 (1985)]. Lipocortins are believed to exert their anti-inflammatory effect by inhibiting phospholipase $A_2$ [F. Hirata et al., "A Phospholipase $A_2$ Inhibitory Protein In Rabbit Neutrophils Induced By Glucocorticoids" *Proc. Nat. Acad. Sci USA*, 77, No. 5, pp. 2533–36 (1980)]. The enzyme phospholipase $A_2$ acts on membrane phospholipids to release arachadonic acid, a precursor in the synthesis of compounds such as prostaglandins, hydroxy-acids and leukotrienes, that are involved in the inflammatory response.

While many studies have been performed with crude protein preparations, recent studies with purified lipocortins have confirmed that these proteins are potent inhibitors of the production of mediators of inflammation [B. Rothhut et al., "Purification And Characterization Of A 32 kDa Phospholipase $A_2$ Inhibitory Protein (Lipocortin) From Human Peripheral Blood Mononuclear Cells", *FEBS Letters*, 219, pp. 169–75 (1987)]. Moreover, recombinant lipocortins have been shown to inhibit the action of phospholipase in in vitro assays [G. Cirino et al., "Recombinant Human Lipocortin 1 Inhibits Thromboxane Release From Guinea-Pig Isolated Perfused Lung", *Nature*, 328, pp. 270–2 (1987); G. Cirino and R. J. Flower, "Human Recombinant Lipocortin 1 Inhibits Prostacyclin Production By Human Umbilical Artery In Vitro" *Prostaglandins*, 34, pp. 59–62 (1987)] and in an in vivo model of the inflammatory response [G. Cirino et al., "Human Recombinant Lipocortin I Has Acutal Local Anti-Inflammatory Properties In The Rat Paw Edema Test", *Proc. Nat. Acad. Sci. U.S.A.*, 86, pp. 3428–32 (1989)].

As a result of their demonstrated anti-inflammatory action, lipocortins should prove useful in the treatment of disorders characterized by inflammatory processes. Examples include arthritic, allergic, dermatologic, ophthalmic and collagen diseases. Furthermore, the use of lipocortins may eliminate side effects associated with currently available anti-inflammatory treatments.

To date, related lipocortin proteins with molecular weights of about 70, 55, 40, 30 and 15 kd have been detected in a variety of animal tissues. K-S Huang et al., "Two Human 35 kd Inhibitors Of Phospholipase $A_2$ Are Related To Substrates Of pp60v-src And Of The EGF Receptor/Kinase", *Cell*, 46, pp. 191–99 (1986). However lack of structural studies has hampered the precise delineation of the family of lipocortins.

Recombinant DNA technology holds significant promise for progress in this field. In the first place, it will help to define the scope of the family of lipocortins, by allowing elucidation of the primary structure of the member proteins. Second, it is desirable to be able to prepare large quantities of lipocortins using recombinant DNA technology. Although it is possible to purify lipocortins from biological sources, production by recombinant methods is more economical. In addition, recombinant methods allow large scale synthesis of desired fragments or otherwise modified versions of native lipocortins.

Two lipocortin genes have been cloned previously [Wallner et al., "Cloning And Expression Of Human Lipocortin, A Phospholipase $A_2$ Inhibitor With Potential Anti-Inflammatory Activity", *Nature*, 320, pp. 77–80, 1986; Huang et al. 1986; C. J. M. Saris et al, "The Sequence Of The cDNA For The Protein Kinase Substrate, p36, Reveals a Multidomain Protein With Internal Repeats", *Cell*, 46, pp. 201–12 (1986)]. Both encode homologous 38 kd proteins with 50% amino acid homology. These two proteins have been termed lipocortin-I and lipocortin-II by Huang et al., 1986.

SUMMARY OF THE INVENTION

The present invention includes recombinant DNA molecules characterized by DNA sequences coding for lipocortins III IV, V and VI, and processes for producing these proteins in hosts transformed with these DNA sequences.

The DNA sequences of this invention include λHLipo III-5, and λHLipo V-1, DNA sequences which hybridize with these DNA inserts and which code on expression for human lipocortins and DNA sequences which code on expression for a polypeptide coded for on expression by any of the foregoing DNA sequences. The DNA sequences of this invention also include DNA sequences that code for lipocortins IV and VI, DNA sequences that hybridize to them and code for a lipocortin and DNA sequences degenerate to any of those sequences.

Recombinant DNA molecules containing these sequences, hosts transformed with them and lipocortins III, IV, V and VI are also part of this invention.

The DNA sequences, recombinant DNA molecules, hosts and processes of this invention enable the production of lipocortins III, IV, V, and VI for use in the treatement of arthritic, allergic, dermatologic, ophthalmic and collagen diseases, involving inflammatory processes.

BRIEF DESCRIPTION OF THE DRAWINGS

FIG. 3 shows the complete nucleotide sequence for human lipocortin-III determined by analysis of λHLipo III-5, and the predicted amino acid sequence of the corresponding protein.

FIG. 4 shows the complete nucleotide sequence for human lipocortin V determined by analysis of λHLipo V-1, and the predicted amino acid sequence of the corresponding protein.

Lane 1† shows the gel profile of the intact and 33 kd (Lane 1) forms of recombinant human lipocortin I, while lanes 2 through 6 show gel profiles of the five purified bovine proteins (lipocortins II through VI). Lane numbers identify the individual family members.

Figure 5:
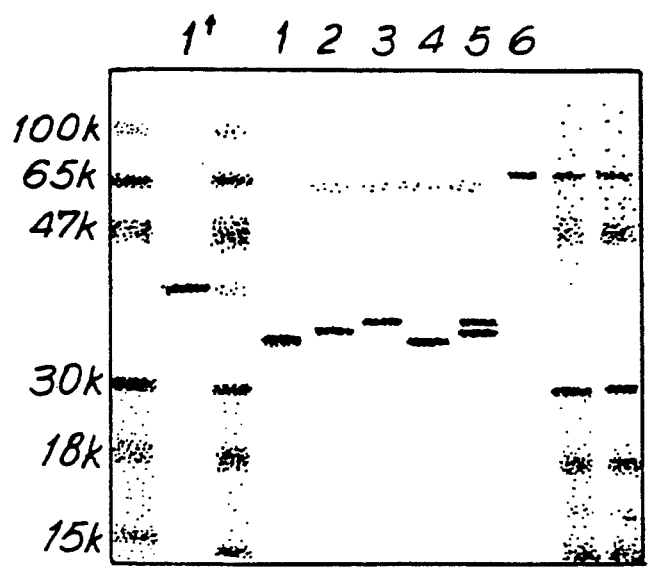
FIG. 5 displays an analysis of lipocortins isolated from bovine intestinal mucosa by SDS-Page.
Figure 6:
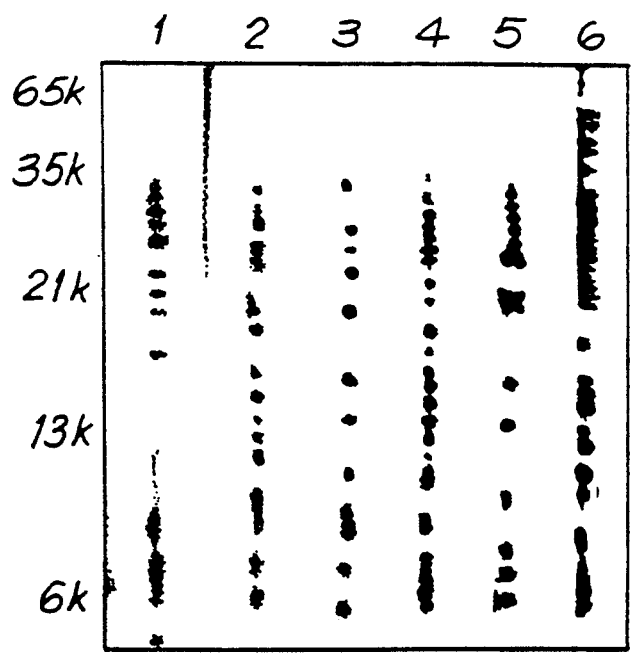

FIG. 6 shows peptide maps of cyanogen bromide fragments of human and bovine intestinal lipocortins from the gel shown in FIG. 5. Peptide fragments were visualized by silver staining. Lane numbers identify the individual family members.

FIG. 7 displays tryptic maps of bovine lipocortins. HPLC-purified bovine lipocortins were digested with trypsin as described by Huang et al., 1986 and separated by reverse phase HPLC on a narrow bore $C_8$ column. The identity of the individual lipocortins is indicated in the figure.

Figure 8:
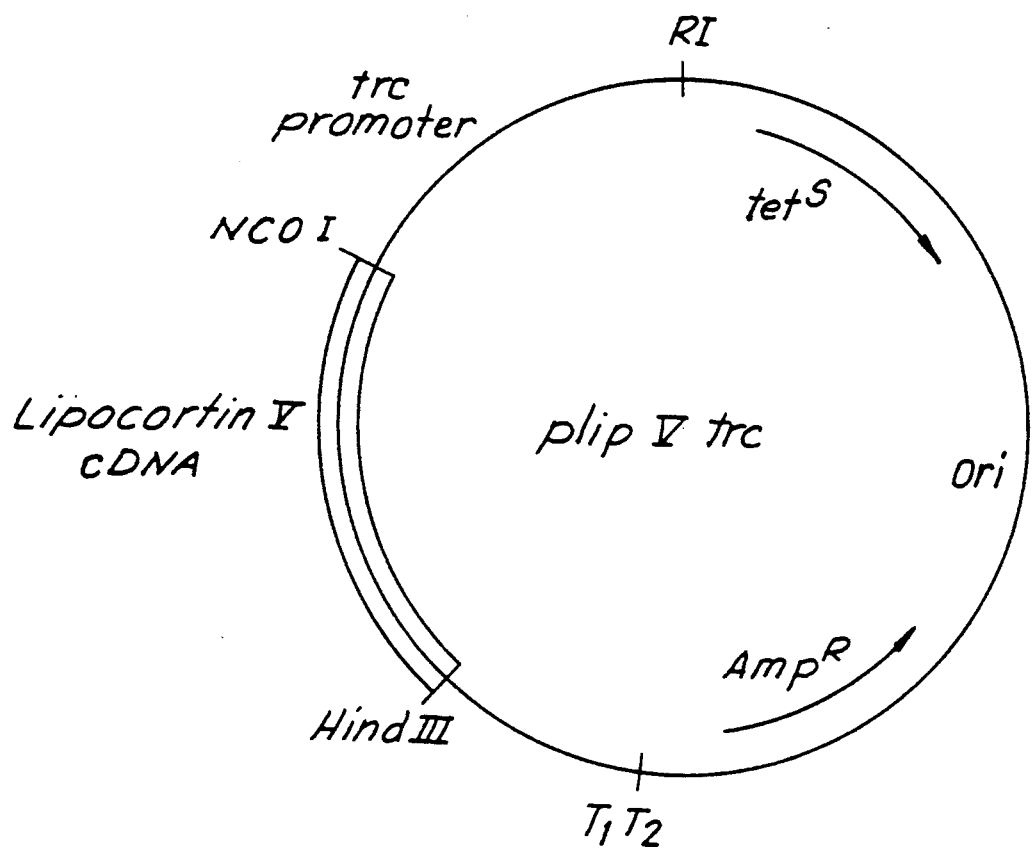

FIG. 8 shows the construction of an expression vector for lipocortin V.

DETAILED DESCRIPTION OF THE INVENTION

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG–Ala-Gly-Cys-Lys

G CTG GTT GTA AG–Leu-Val-Val

GC TGG TTG TAA G–Trp-Leu-(STOP)

Polypeptide—A linear array of amino acids connected one to the other by peptide bonds between the α-amino and carboxy groups of adjacent amino acids.

Peptidase—An enzyme which hydrolyzes peptide bonds.

Genome—The entire DNA of a cell or a virus. It includes, inter alia, the structural gene coding for the polypeptides of the substance, as well as operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TET ®) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

Lipocortin —a protein which inhibits the enzyme phospholipase $A_2$ and has at least one copy of the consensus sequence comprising substantially the amino acid sequence: MetLysGlyLeuGlyThrAspGlu AspThrLeuIleGluIleLeuThrSerArg.

The present invention relates to DNA sequences and recombinant DNA molecules coding for lipocortins III, IV, V, and VI, and processes for the production of those polypeptides.

Although a variey of selection and DNA cloning techniques might potentially have been employed in our isolation and cloning of the DNA sequences of this invention, in one embodiment of the invention, we adopted a selection strategy based upon rat lipocortins. Accordingly, we purified rat lipocortins III and V from the extracellular supernatant of rat peritoneal exudate cells and determined the amino acid sequence of various fragments of those proteins. Based on those protein sequences, we then synthesized several antisense oligonucleotide DNA probes corresponding to those regions of purified rat protein which had minimal nucleotide degeneracy. We then used these probes to screen a rat cDNA library comprising *E.coli* cells containing cDNA sequences inserted into a phage cloning vector.

For screening, we hybridized the oligonucleotide probes to a rat lung cDNA library utilizing a plaque hybridization screening assay and we selected clones hybridizing to a number of our probes. After isolating and subcloning the selected rat cDNA inserts into plasmids, we determined their nucleotide sequences and compared them to our amino acid sequences from peptides of purified rat lipocortin. As a result of this comparison, we found that the nucleotide sequences of the clones isolated coded for amino acid sequences that were identical to the amino acid sequences of peptides from our purified rat lipocortins. We then used various restriction fragments from the rat cDNAs as hybridization probes to screen the respective human cDNA libraries. We confirmed that the clones isolated contained the full length sequence encoding human lipocortins III and V by comparing the sequences with the known sequences of human Lipocortin I and II, by checking the position of the start and stop codons in the proper reading frames, and by considering the expected size of the protein.

The cDNA sequences of this invention can be operatively linked to expression control sequences and used in various mammalian or other eukaryotic or prokaryotic host cells to produce the human lipocortin polypeptides coded for by them.

According to a second embodiment of this invention, we isolated from bovine intestinal mucosa lipocortins IV and VI. We determined the amino acid sequences of tryptic fragments of these polypeptides. Synthetic DNA probes can be made based on the amino acid sequence data, and the probes can be used to screen a bovine library for the cDNA's coding for lipocortins IV and VI. The human cDNAs can be isolated using bovine CDNAs as probes in the same manner as described for lipocortins III and V. The complete sequence of human lipocortin IV and VI can then be determined by sequencing the cDNA thus isolated. Furthermore, the cDNA can be used in eukaryotic and prokaryotic host cells to express the lipocortin proteins.

The human lipocortins produced by the methods of this invention are useful as anti-inflammatory agents and in anti-inflammatory methods and therapies. For example, such compositions may comprise an amount of a lipocortin which is pharmaceutically effective to reduce inflammation and a pharmaceutically acceptable carrier. Such therapies generally comprise a method of treating patients in a pharmaceutically acceptable manner with those compositions.

MATERIALS AND METHODS

A wide variety of host/cloning vehicle combinations may be employed in cloning or expressing the DNA sequences coding the human lipocortins in accordance with this invention. For example, useful cloning or expression vehicles may consist of segments of chromosomal and synthetic DNA sequences, such as various known derivatives of SV40 and known bacterial plasmids, e.g. plasmids from *E.coli* including colE1, pCR1, pBR322, pMB9 and their derivatives; wider host range plasmids, e.g., RP4, phage DNAs, e.g., the numerous derivatives of phage λ, e.g., NM 989; and other DNA phages, e.g., M13 and filamentous single stranded DNA phages and vectors derived from combinations of plasmids and phage DNAs such as plasmids which have been modified to employ phage DNA or other expression control sequences or yeast plasmids such as the 2μ plasmid or derivatives thereof.

Within each specific cloning or expression vehicle, various sites may be selected for insertion of the human lipocortin protein DNA sequences of this invention. These sites are usually designated by the restriction endonuclease which cuts them and are well recognized by those of skill in the art. Various methods for inserting DNA sequences into these sites to form recombinant DNA molecues are also well known. These include, for example, dG-dC or dA-dT tailing, direct litigation, synthetic linkers, exonuclease and polymerase-linked reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragement by alternative means.

Various expression control sequences may also be chosen to effect the expression of the DNA sequences of this invention. These expression control sequences include, for example the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast alpha-mating factors, or actin, promoters for mammalian cells such as the SV40 early promoter, adenovirus late promoter, and metallothionine promoter, and other sequences known to control the expression of genes of prokaryotic or eukaryotic cells, their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the chosen human lipocortin DNA sequence is inserted into a cloning vehicle, enables the expression control sequences to control and promote the expression of the DNA sequences.

The vector or expression vehicle and, in particular, the sites chosen therein for insertion of the selected DNA fragment and the expression control sequence employed in this invention, are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular lipocortin sequence is determined by a balance of these factors, not all selections being equally effective for a given case.

It should also be understood that the DNA sequence coding for the lipocortin proteins of this invention which are inserted at the selected site of a cloning or expression vehicle may include nucleotides which are not part of the actual gene coding for the desired lipocortin or may include only a fragment of the entire gene for that protein. It is only required that whatever DNA sequence is employed, a transformed host will produce a lipocortin protein. For example, the lipocortin DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combination of them. Such constructions may aid in expression of the desired lipcortin DNA sequence, improve purification or permit secretion, and preferably maturation, of the lipocortin from the host cell. The lipocortin DNA sequence may alternatively include an ATG start codon, alone or together with other codons, fused directly to the sequence encoding the first amino acid of a mature native lipocortin. Such constructions enable the production of, for example a methionyl or other peptidyl lipocortin that is part of the invention. The N-terminal methionine or peptide may then be cleaved intra- or extracellularly by a variety of known processes or the polypeptide used together with the methionine attached to the peptide in the anti-inflammatory compositions and methods of this invention. The lipocortin may also be used directly without cleavage of that or other peptide presequence.

The cloning vehicle or expression vector containing the lipocortin coding sequence of this invention is employed in accordance with this invention to transform an appropriate host so as to permit that host to express the lipocortin protein for which the DNA sequence codes.

Useful cloning or expression hosts include strains of *E.coli*, such as *E.coli* W3110I$^Q$, *E.coli* Ja221, *E.coli* ED8767, *E.coli* DH1, *E.coli* LE392, *E.coli* HB101, *E.coli* X1776, *E.coli* X2282, and insect cells, Streptomyces, yeasts and other fungi, animal hosts such as CHO cells or mouse cells, other animal (including human) hosts, plant cells in culture or other hosts.

The selection of an appropriate host is also controlled by a number of factors recognized by the art. These include, for example, compatibility with the chosen vector, toxicity of the proteins encoded by the hybrid plasmid, susceptibility of the desired protein to proteolytic degradation by host cell enzymes, contamination or binding of the protein to be expressed by host cell proteins that are difficult to remove during purification, ease of recovery of the desired protein, expression characteristic, bio-safety and cost. A balance of these factors must be struck with the understanding that not all host vector combinations may be equally effective for either the cloning or expression of a particular recombinant DNA molecule.

It should be understood that the human lipocortins prepared in accordance with this invention may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of lipocortin proteins (e.g. starting with all or parts of a lipocortin signal sequence or other eukaryotic or prokaryotic signal sequences), in the form of a mature lipocortin or in the form of a f-met-lipocortin (i.e., a lipocortin in which the initiating methionine has not been removed).

One particularly useful form of a protein in accordance with this invention, or at least a precursor thereof, is a mature lipocortin with an easily cleaved amino acid or series of amino acids attached to the amino terminus. Such construction allows synthesis of the protein in an appropriate host, where a start signal that may not be present in the mature lipocortin is needed, and the cleavage in vivo or in vitro of the extra amino acids to produce mature lipocortins. Such methods exist in the art. See, e.g., U.S. Pat. Nos. 4,332,892; 4,338,397; and 4,425,437. The polypeptides may also be glycosylated, unglycosylated, or have a glycosylation pattern different than that of native lipocortins. Such glycosylation patterns will result from the host cell or post-expression treatment chosen for the particular lipocortin.

The proteins of this invention also include biologically active polypeptide fragments derived from lipocortins by treatment with proteases or by expression of a fragment of the DNA sequence which codes for a lipocortin. The proteins of this invention also include lipocortins that are coded for on expression by DNA sequences characterized by different codons for some or all of the codons of the present DNA sequences. These substituted codons may code for amino acids identical to those coded for by the codons replaced and result in higher yield of the polypeptide. Alternatively, the replacement of one or a combination of codons leading to amino acid replacement or to a longer or shorter lipocortin may alter its properties in a useful way. For example, the alteration may increase the stability, increase the solubility or increase the therapeutic efficacy.

In order that this invention may be better understood, the following examples are set forth. These examples are for purposes of illustration only and are not to be construed as limiting the scope of the invention in any manner.

EXAMPLES

A. Purification of Rat Lipocortins III and V

Rat peritoneal lavages were prepared as described previously. [R. B. Pepinsky et al., "Purification And Partial Sequence Analysis Of A 37-kDa Protein That Inhibits Phospholipase A$_2$ Activity From Rat Peritoneal Exudates", *J. Biol. Chem.*, 261, pp. 4239–46 (1986)].

Dialyzed lavages were quick frozen with liquid nitrogen and stored at −70° C. Batches representing 125 rat lavages were processed. Particulate material was removed by centrifugation (10,000 rpm-GSA rotor) for 30 minutes, and the supernatant was subjected to DEAE-cellulose column chromatogrpahy (DE52 Whatman, 2.5×15 cm) in 25 mM Tris-HCl at pH 7.7. Bound proteins were eluted with a gradient of NaCl (0–0.3M) in the same buffer. Fractions of 18 ml were collected and monitored for absorbance at 280 nm and for phospholipase $A_2$ inhibitory activity as described by Pepinsky et al., 1986 and set forth below.

The substrate for phospholipase $A_2$, autoclaved [$^3$H]oleic acid-labeled *Escherichia coli*, was prepared as follows: Membrane phospholipids of *E.coli* were labeled by incorporating [$^3$H]oleic acid (10 Ci/mmole), into their medium during their exponential growth phase. The labeled *E.coli* were then killed by autoclaving and recovered by centrifugation, washed repeatedly in Tris buffer (200 mM, pH 8) containing 10 mg/ml bovine serum albumin. When the washings contained negligible radioactivity, this substrate was stored at 4° C. in the same buffer + 1.0% sodium azide and used as required as an exogenous substrate for the phospholipase $A_2$ assay.

Samples were tested for phospholipase $A_2$ inhibitory activity as follows: For each experimental point, 200 µl of sample was combined with 50 µl of a 7X buffer (0.7M Tris-HCl, pH 8.0, 60 mM $CaCl_2$) and 50 µl of a dilute preparation of porcine pancreatic phospholipase $A_2$ (Sigma) that contained 100 ng of enzyme and 125 µg of bovine serum albumin. Samples were mixed and kept on ice for 1 h. 25 µl of the substrate was added, and the reaction was performed at 6° C. for 8 min. The reaction was stopped by adding 100 µl of 2N HCl and 100 µl of 20 mg/ml delipidated bovine serum albumin (Sigma) to each tube. Tubes were held on ice for 30 min and *E.coli* pelleted by centrifugation for 5 min at 10,000×g. 250 µl of each supernatent was mixed with 4 ml of scintillation fluid and the residual phospholipase activity quantitated by liquid scintillation counting. In all analyses, samples were assayed in duplicate and adjusted for nonspecific release by subtracting a control value in which the preparations were assayed without phospholipase $A_2$. One unit of activity inhibits 15 ng of phospholipase $A_2$. Two inhibitory peaks of protein that eluted withe NaCl were detected. Both were subjected to sequential chromatography steps involving gel filtration and fast protein liquid chromatogrpahy (FPLC) on a Mono S cation exchange resin (HR 5/5, Pharmacia). For gel filtration, the inhibitory peaks were concentrated to 5 ml by ultrafiltration and loaded onto a P150 column (BioRad, 2.5×40 cm) in 25 mM Tris-HCl at pH 7.7. Five ml fractions were collected. Both inhibitors eluted as single peaks. Lipocortin-V eluted with an apparent mass of 30 kd, while lipocortin-III migrated anomalously as if it were only 20 kd. Active gel filtration fractions were processed by FPLC essentially as described by Huang et al. 1986. Lipocortin-V flowed through the cation exchange matrix, while lipocortin-III bound to the Mono S matrix and was eluted with 100 mM NaCl. Typically, from one batch of rat lavages we recovered 50 µg of lipocortin-III and 200 µg of lipocortin-V.

For structural studies FPLC-purified samples were lyophilized, dialyzed against 0.1% SDS, and subjected to preparative polyacrylamide gel electrophoresis in SDS. Appropriate bands were excised with a razor blade and the proteins were electroeluted from the gel [M. W. Hunkapiller and L. E. Hood, "Analysis Of Phenylthiohydantoins By Ultrasensitve Gradient High Performance Liquid Chromatography", *Meth. Enzymol.* 91, pp. 486–93 (1985)]. Sixty µg aliquots of each preparation were precipitated with 20% trichloroacetic acid and washed as described by Pepinsky et al., 1986. The dried pellets were suspended in 400 µl of 0.1M ammonium bicarbonate, 0.1 mM $CaCl_2$ and incubated with 3 ug of trypsin for 16 h at 37° C. Trypsin was added in three equal aliquots; the first at time zero, the second after 4 h, and the third after 12 h. The digests were acidified with formic acid to 20% and the fragments fractionated by reverse phase high pressure liquid chromatography on a $C_{18}$ column (0.46×25 cm, Spectrophysics) at 39° C. with a flow rate of 1.4 ml/min. Peptides were eluted with a gradient of acetonitrile (0–75%) in 0.1% trifluoroacetic acid. Column eluates were monitored at 214 nm. Peak fractions were subjected to sequence analysis in an Applied Biosystems 470A gas phase sequencer in the presence of polybrene [Hewick et al., "A Gas-Liquid Solid Phase Peptide And Protein Sequenator", *J. Biol. Chem.*, 256, pp. 7990–7 (1981)]. PTH-amino acids were identified on-line using an Applied Biosystems 120A PTH analyzer.

B. Lipocortin Antisera

Antisera against recombinant human lipocortin-I and against human placental lipocortin-II were prepared as previously described. [Huang et al., 1986; R. B Pepinsky, and L. K. Sinclair, "Epidermal Growth Factor-Dependent Phosphorylation Of Lipocortin", *Nature*, 321, pp. 81–4 (1986)]. Antisera against rat lipocortin-V were produced in rabbits using the lymph node immunization procedure. [M. B. Sigel et al., "Production Of Antibodies By Inoculation Into Lymph Nodes, *Methods Enzymol.*, 93, pp. 3–12 (1983)]. Electroeluted lipocortin-V (50 ug per rabbit) emulsified in complete Freund's adjuvant was used as the immunogen.

C. Characterization of Rat Lipocortins III and V

Figure 1:
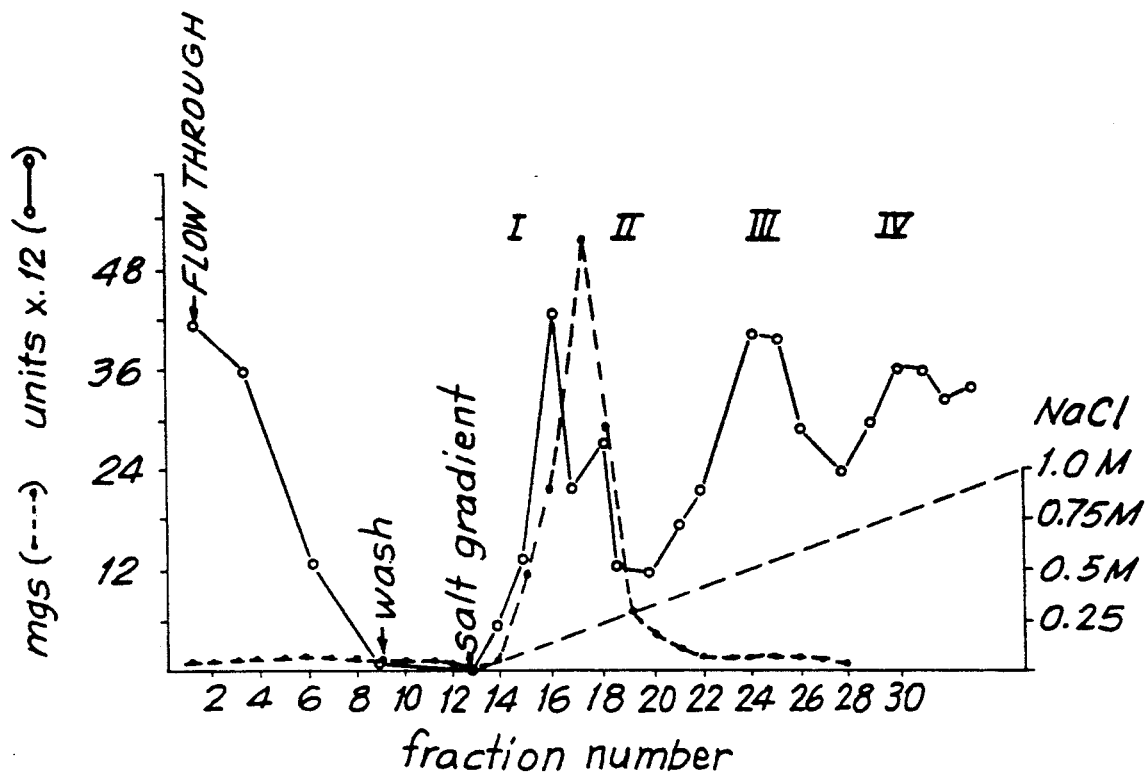
FIG. 1 is a plot of the absorbance of fractions collected from a DEAE-cellulose column loaded with non-particulate extract from pooled rat peritoneal lavages. Solid lines indicate phospholipase $A_2$ inhibitory activity. Broken lines indicate total protein.

When rat peritoneal lavage preparations were subjected to DEAE-cellulose chromatography, five peaks of phospholipase $A_2$ inhibitory activity were observed. FIG. 1 shows results from such an analysis. The major activity peak is the flow-through fraction, which was used previously as a source of lipocortin-I. Pepinsky et al., 1986. Four other peaks were eluted with salt. Here, we have studied in detail the two activity peaks that eluted with 125 mM NaCl (I) and with 225 mM NaCl (II). Peaks I and II both contained proteins that were found by sequencing to share homologous amino acid sequences with the previously known lipocortin sequences (lipocortins I and II). We refer to the peak I inhibitor as lipocortin-III and the peak II in hibitor as lipocortin-V. To improve the efficiency of the DEA step during preparative purifications of the peak I and II activities, the inhibitors were eluted with a shallow salt gradient from 0 to 0.3M NaCl. Each inhibitory peak was then subjected to sequential chromatography steps using gel filtration and Mono S FPLC matrices. Analysis by SDS-PAGE showed that both final preparations contained a single major 35 kd protein. The specific activities of the inhibitors in an in vitro phospholipase $A_2$ inhibition assay using porcine pancreatic phospholipase $A_2$ as an enzyme source both were 10,000 units/mg and thus were comparable to the specific activities observed previously for lipocortins I and II. Huang et al., 1986; Pepinsky et al., 1986.

Figure 2:
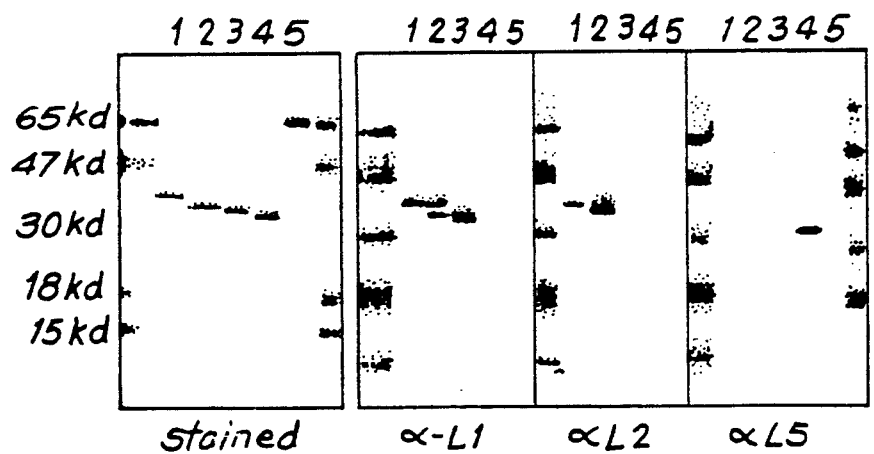
FIG. 2 displays an analysis of purified rat peritoneal proteins shown to have an inhibitory effect on phospholipase $A_2$ by polyacrylamide electroephoresis in SDS ("SDS-Page"). The proteins were either stained with Coomassie blue or subjected to Western blotting with antisera to lipocortins. Lanes 1, 3 and 4 were loaded with rat lipocortins I, III and V respectively and lanes 2 and 5 were loaded with bovine lipocortins II and VI.

FIG. 2 shows gel profiles of purified rat lipocortin-III (lane 3) and rat lipocortin-V (lane 4) stained with Coomassie blue. For comparative purposes, rat lipocortin-I (lane 1) and bovine lipocortins II and VI (lanes 2 and 5) are also presented. The remainder of the panel shows blots of the same preparations probed with antisera against lipocortin-I ($\alpha$-L1), lipocortin-II ($\alpha$-L2), and lipocortin-V ($\alpha$-L5). While the lipocortin-V antiserum is specific for lipocortin-V, the lipocortin-I antiserum has a low titer of antibodies that recognize lipocortin-II and the lipocortin-II antiserum has a low filter of antibodies that recognize lipocortin-I. The lipocortin-I antiserum, which was raised against recombinant protein, has a high titer towards rat lipocortin-III. To verify that the immunoreactive component in the lipocortin-III preparation is lipocortin-III and not a fragment of lipocortin-I, rat lipocortins I and III were subject to CNBr mapping where cleavage products were detected by Western blotting using lipocortin-I antisera to visualize immunoreactive fragments. The two profiles were different. All of the lipocortin-III fragments were compared by this procedure and found to be similar.

D. Isolation and Sequencing of Genes Coding for Human Lipocortins III and V

Oligonucleotide probes were synthesized on an Applied Biosystems 380A DNA synthesizer and purified by gel electrophoresis. [M. D. Matteucci and M. H. Carruthers, "Synthesis Of Deoxyoligonucleotides On A Polymer Support", *J. Am. Chem. Soc.*, 103, pp. 3185-91 (1981)]. Oligonucleotides were end-labeled with polynucleotide kinase and [$\gamma$-$^{32}$P]-ATP and purified by gel electrophoresis. [A. Maxam and W. Gilbert, "Sequencing End-Labeled DNA With Base-Specific Chemical Cleavages". *Meth. Enzym.*, 65, pp. 499-560 (1980)]. Oligonucleotide probe pool RLip 4-6 is a 20-mer with 256 fold degeneracy based on tryptic peptide T26* (AspLeuValAsnAspMetLys) of rat lipocortin-V. To decrease the degeneracy of the probes, they were synthesized in 4 subpools of 64 fold degeneracy each. Individual subpools were hybridized to rat lung poly(A) RNA in a Northern blot analysis as described previously by Wallner et al., 1986. For rat lipocortin-III, two sets of probe pools were used, ELip 1-4 and ELip 5-8. ELip 1-4 is a 17-mer with 128 fold degeneracy based on tryptic peptide T2 (GlyAlaGlyThrAspGluPheThrLeuAsn Arg) and ELip 5-8 is a 20-mer that is 512 fold degenerate and based on fragment T3 (GluIleSerGln AlaTyrTyrThrAlaTyrLys). Both were synthesized in 4 subpools. For both proteins, individual subpools that hybridized to a transcript of approximately 1800 nucleotides under stringent conditions were used to screen a rat lung $\lambda$gt10 cDNA library which was constructed from rat lung poly(A) RNA essentially as described previously. Wallner et al., 1986. Positive phage, $\lambda$RLipo III-5 for rat lipocortin III and $\lambda$RLipo V-1 for rat lipocortin-V, which contained the respective full length cDNAs, were subcloned into plasmid pNN01 and pNN09 respectively and the DNA sequences determined by the method of Maxam and Gilbert (1980) and by the related method of G. M. Church and W. Gilbert, "Genomic Sequencing, *Pro. Natl. Acad. Sci. USA*. 81, pp. 1991-95 (1984).

*"T_" refers to tryptic fragments of the purified rat lipocortin isolated by reverse phase HPLC on a $C_{18}$ column as described previously. Fragments were subsequently sequenced with a gas phase sequencer also as previously described.

Human lipocortin-III was isolated from a $\lambda$gt11 human lung cDNA library obtained from Clonetech Laboratories by using the complete rat lipocortin-III cDNA insert of $\lambda$RLipo III-5 as a hybridization probe. Human lipocortin-V cDNA was isolated by screening a $\lambda$gt10 human peripheral blood lymphocyte cDNA library with the complete rat lipocortin-V cDNA insert of $\lambda$RLipo V-1.

The cDNA library was constructed from lymphocyte poly (A) RNA (cells were stimulated with interferon-$\gamma$ and phytohemaglutinin). Screening procedures were performed essentially as described by Wallner et al., 1986 except that the temperature of the washes and filters was kept at 55° C. to allow for cross-species nucleotide mismatches. The complete DNA sequences of human cDNA clones for lipocortin-III ($\lambda$HLipo III-5) and lipocortin-V ($\lambda$HLipo V-1) were determined as described above, and are shown in FIGS. 3 and 4, respectively.

In addition to disclosing the full length sequences for both human lipocortin III and V, FIGS. 3 and 4 also display the deduced amino acids sequences for the corresponding proteins. The cDNA clone for human lipocortin-III (1339 bp) contains 46 bp of 5' and 324 bp of 3' untranslated sequences, and encodes a protein of 323 amino acids. The clone for lipocortin-V (1574 bp) contains 142 bp of 5' and 472 bp of 3' untranslated sequences, and encodes a protein of 320 amino acids. Although we have not determined the amino terminus of the mature proteins because they were blocked, we believe that the intiating methionine in lipocortin III is coded for by ATG at position 47 of the human gene. This is based on comparison of the amino acid sequence deduced for human lipocortin III with that of lipocortin I and II, where the location of the initiating methionine has been determined. For the same reasons, we believe that the initiating methionine of lipocortin-V is coded for by the ATG at position 143 of the human gene.

We subcloned $\lambda$HLipo III-5 and $\lambda$HLipo V-1 into the *E.coli* pUC plasmids pNN01 and pNN09 to create plasmids designated pHLipo III-3-5 and pHLipo V-3b, respectively. Microorganisms prepared by the processes described herein are exemplified by a culture deposited in the cuture collection of In Vitro, International, Linthicum, Md. The cultures were deposited on Feb. 18, 1988 and are designated as follows:

*E.coli* MC 1061: hLipo III-3-5 IVI No. 10158 (lipocortin III)

*E.coli* MC 1061: hLipo V-3b IVI No. 10159 (lipocortin V)

E. Isolation and Characterization of Lipocortins From Bovine Intestinal Mucosa We isolated lipocortins from bovine sources and characterized them by peptide mapping and sequence analysis. Bovine proteins were extracted from calf small intestine using the procedure of V. Gerke and K. Weber (1984). "Identity Of p36K Phosphorylated Upon Rous Sarcoma Virus Transformation With A Protein Purified From Brush Borders; Calcium-Dependent Binding To Non-Erythroid Spectrin And F-actin", *EMBO J.*, 3, pp. 227-33 (1984). The EGTA extract was dialyzed against 10 mM Imidazole-HCl pH 7.5, 1 mM $NaN_3$, 0.1 mM EDTA and subjected to DEAE-cellulose chromatography. Bound proteins were eluted with a gradient of NaCl (0-0.3M) in the same buffer. Three peaks of phospholipase $A_2$ inhibitory activity were detected, which correspond to the flow-through fraction and peaks I and II from the rat peritoneal lavage preparation. Each peak was subjected to cation-exchange chromatography on fast flow S-Sepharose (Pharmacia). Bound proteins were eluted with 0-0.2M NaCl in 50 mM MES pH 6.5, 1 mM EDTA. For Fast S chromatography of the DEAE-cellulose flow-through peak, the preparation was first concentrated 10-fold by ultrafiltration and diluted 1:1 with 50 mM MES pH 6.0. A single peak of activity was eluted with salt. For fractionation of the peak I and II activities, the inhibitory fractions were diluted 4-fold with 25 mM MES pH 6.0. Both preparations contained two inhibitors; one flowed through the ion-exchange matrix, the other bound to Fast S and was eluted with salt. Each inhibitor was shown to be a unique protein by peptide mapping and immunological analyses.

Previously, we confirmed that the predominant inhibitor in the DEAE flow-through fraction from bovine intestine was lipocortin-II. [Huang et al., 1986]. Here, by the same criteria, we determined that the bovine peak I inhibitor that bound the Fast S matrix corresponds to rat lipocortin-III and the peak II inhibitor that flowed through Fast S corresponds to rat lipocortin-V. For simplicity, we refer to the Peak I inhibitor that flowed through Fast S as lipocortin-IV and the peak II inhibitor that bound to Fast S as lipocortin-VI. The schematic shown below summarizes the steps used for purification of the bovine lipocortins.

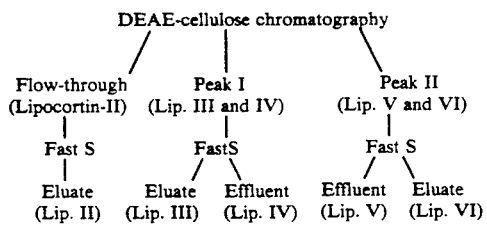

For structural studies and as a final measure of purity, the various inhibitors were subjected to reverse phase high pressure liquid chromatography on a $C_4$ column. Each inhibitor exhibited a different elution profile, which we now use as a method of identification. FIG. 5 shows gel profiles of the purified inhibitors. The 33 kd fragment of bovine lipocortin-II (lane 2) and bovine lipocortins III–V (lanes 3–5) all have similar electrophoretic mobilities. Recombinant human lipocortin-I (lane 1¶) and the 33 kd fragment of human lipocortin-I (lane 1) are also presented. We infer that the two bands in lane 5 are derived from a single protein since both species react with rat lipocortin-V antisera and both have similar peptide maps when subjected to CNBr mapping.

FIG. 6 shows CNBr peptide maps for each of the bovine proteins and for the 33 kd fragment of human lipocortin-I. Each profile is distinct and thus can be used for identifying the individual family members. Only the cleavage profile for the smaller form of lipocortin-V is presented.

FIG. 7 shows tryptic peptide maps of the five bovine proteins. Like the CNBr cleavage profiles, the tryptic peptide maps confirm that five distinct lipocortins were isolated from bovine intestinal mucosa. While chromatographic properties indicate the identities of the various proteins, because of the complexity, each protein was characterized further by sequence analysis. Table I shows representative sets of sequences for lipocortin IV and lipocortin VI using the tryptic fragments that were shown in FIG. 7. Individual fragment numbers refer to the fraction numbers presented in FIG. 7.

TABLE I a. Lipocortin-IV:
| | |
|---|---|
| T60: | SerAspThrSerPheMetPheGlnArg |
| T68: | AspGluSerAsnTyrLeuAspAspAlaLeuMetArg |
| T69: | AsnHisLeuLeuHisValPheAspGluTyrLysArg |
| T87: | GlyLeuGlyThrAspGluAspAlaIleIleAsnVal LeuAlaThrArg |
| T89: | SerGluLeuSerGlyAsnPheGluGlnValIleLeuGly |
| T112: | SerGluLeuSerGlyAsnPheGluGlnValIleLeuGly MetMetThrProThrValLeuTyrAspValGlnGlu | b. Lipocortin-VI:
| | |
|---|---|
| T50: | SerThrAlaGluTyrPheAlaGluArg |
| T51: | GlyThrValArgProAlaGlyAspPheAsnProAspAla AspAlaValLys |
| T52: | MetThrAsnTyrAspValGluHisThrIleLys |
| T59: | ValPheGlnGluPheValLys |
| T61: | ArgValPheGlnGluPheValLys |
| T70: | GlnMetTrpGluLeuSerAlaValAlaArg |
| T81: | AspValPheValAlaIleValGlnSerValLys GluAlaIleLeuGluLeuIleThr |
| T83: | LeuIleLeuIleLeuMetMetProIleAlaIleTyrAsn Ala |
| T86: | AspPheProAspPheAsnProSerGlnAspAlaGluThr LeuTyrAsnAlaMetLys |
| T88: | GlyLeuGlyThrAspGluAspThrIleIleAspIleIle AlaHis |
| T98: | MetLeuValValLeuLeuGlnGlyThrArgGluGluAsp AspValValSerGluAspLeuValGlnGln |

We have identified 150 amino acids of sequence information for lipocortin VI, accounting for approximately 25% of its primary structure. Like sequences for lipocortins I–V,, the partial sequences of lipocortin-VI clearly indicate that it shares homology with those other lipocortins. Identities of the sequences ranged from 27% with lipocortin-III to 37% with lipocortin-V. Over the same region lipocortin I and II sequences showed 49% identity. In particular, the amino acid sequence of fraction T88 conforms with the consensus sequence, which we have found to be characteristic of the lipocortin family. [M. J. Geisow and J. H. Walker, "New Proteins Involved Cell Regulation By Calcium And Phospholipids," *Trends in Biochemistry*, 11, pp. 420–23 (1986); R. H. Kretsinger and C. E. Creutz, "Consensus In Exocytosis", *Nature*, 320, 573 (1986)].

Comparison of the amino acid sequences of bovine lipocortins II through VI with corresponding human and rat lipocortins demonstrates high levels of conservation. Lipocortins I, III and V are about 85% conserved across species, while lipocortin II is about 98% conserved. Moreover, the similarity of the amino acid sequences of certain regions of lipocortins coupled with the functional characteristic of phospholipase $A_2$ inhibition is strong evidence that these proteins are members of a single family, and that the family is evolutionarily conserved.

The complete sequence of human lipocortins IV and VI may be obtained using the amino acid sequence of the tryptic fragments we have disclosed here. A characteristic of the lipocortin proteins is that they exhibit conservation across species lines. A common comparison of the nucleotide sequences of the four lipocortins for which sequence data is available for human and for one other species demonstrates a level of homology of about 85–90%, for lipocortins I, III, and V and about 98% for lipocortin II. [R. B. Pepinsky et al., "Five Distinct Calcium And Phopolipid Binding Proteins Share Homology With Lipocortin I" *J. Biol. Chem.*, 263, pp. 10799–811 (1988). Because of this degree of conservation, the amino acid sequences of the tryptic fragments disclosed here can be used, indirectly, to isolate the corresponding human genes for lipocortins IV and VI.

Using the methods disclosed in Wallner et al., 1986, the amino acid sequences of the tryptic fragments we have obtained can be used to synthesize antisense probes against bovine lipocortins IV and VI. Preferrably, these probes can be used to isolate the complete bovine gene for these two lipocortins, by hybridizing the oligonucleotide probes to a complete bovine cDNA library under stringent conditions as previously described for isolation of rat lipocortin cDNAs. Preferrably, the bovine cDNA fragments can then be used to isolate the corresponding human cDNA by hybridizing bovine cDNA probes to a human cDNA library conventional conditions* Pepinsky et al. (submitted).
* Conventional hybridization conditions may be defined as 2 X SET (or equivalent buffer) at 68° C.

Alternatively, antisense probes based on the sequences of the tryptic fragments can be used to probe a human cDNA library directly, without first isolating the corresponding bovine gene, as described by Huang et al., 1986.

The initiating condons for lipocortins IV and VI may be inferred from the nucleotide sequence for the full length molecules as has been done for lipocortins III and V here. All members of the lipocortin family begin with the nucleotide sequence MetAlaMet. Hence the first occurrence of the corresponding codons marks the point of the initiation of translation.

F. Expression of Human Lipocortin V in E.Coli.

We expressed human lipocortin V in *E.coli* using the expression vector pkk233-2, as described in PCT Application WO 86/04094. In this construct, lipocortin V is expressed under the control of the trc promoter. Induction of the promoter is elicited with 2 mM IPTG. The NcoI/HindIII restriction fragment of pHLipoV-3b was inserted into the NcoI/HindIII digested plasmid pkk233-2 using standard procedures. The construction of this plasmid is shown in FIG. 8 schematically. The resulting plasmid was transformed into *E.coli* strain JA221. To express lipocortin V, cells were grown to O.D.$_{550}$ 1.0 and induced by addition of 2 mM IPTG for two hours before harvesting. Cells were pelleted by centrifugation and resuspended in 25 mM Tris-HCl. Cells were passed through a French pressure cell at 12,000 p.s.i. and the protein purified through a combination of chromatography steps, first on DEAE cellulose and subsequently by gel filtration on a P150 column. The purified protein was active in the phopholipase $A_2$ inhibition assay described by Pepinsky et al., 1986, with a specific activity of 10,000 units/mg.

Improving the Yield and Activity of Human Lipocortin-Like Polypeptides Produced in Accordance with this Invention The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus advantageous to separate the specific lipocortin coding sequences of this invention from their adjacent nucleotide sequences and to fuse them instead to other known expression control sequences so as to favor higher levels of expression and production of lipocortin-like polypeptides. This having been achieved, the newly engineered DNA fragments may be inserted into higher copy number plasmids or bacteriophage derivatives in order to increase the number of gene copies within the cell and thereby further to improve the yield of expressed lipocortin-like polypeptides.

Several expression control sequences may be employed as described above. These include the operator, promoter and ribosome binding and interaction sequences (including sequences such as the Shine-Dalgarno sequences) of the lactose operon of *E.coli* ("the lac system"), the corresponding sequences of the tryptophan synthetase system of *E.coli* ("the trp system"), the major operator and promoter regions of phage λ ($O_LP_L$ as described above and $O_RP_R$), a control region of filamentous single-stranded DNA phages, the tac or trc system, the promoter for 3-phosphoglycerate kinase or other glycolytic enzymes, the promoters of acid phosphatase, e.g., Pho5, the promoters of the yeast α-mating factors, promoters for mammalian cells such as the SV40 early and late promoters, adenovirus late promoter and metallothionine promoter, and other sequences which control the expression of genes of prokaryotic or eukaryotic cells and their viruses or combinations thereof.

Therefore, to improve the production of the lipocortin-like polypeptides of this invention, the DNA sequences for those polypeptides may be prepared as before and inserted into a recombinant DNA molecule closer to its former expression control sequence or under the control of one of the above improved expression control sequences. Such methods are known in the art.

Other methods useful to improve the efficiency of translation involve the insertion of chemically or enzymatically prepared oligonucleotides in front of the initiating codon of the lipocortin-related DNA sequences of this invention or the replacement of codons at the N-terminal end of the DNA sequence with those chemically or enzymatically prepared oligonucleotides. By this procedure, a more optimal primary and higher order structure of the messenger RNA can be obtained. More specifically, a sequence can be so designed that the initiating ATG codon occurs in a readily accessible position (i.e., not masked by secondary structure) either at the top of a hairpin or in other single-stranded regions. The position and sequence of the aforementioned Shine-Dalgarno segment can similarly be optimized. The importance of the general structure (folding) of the messenger RNA has been documented [D. Iserentant and W. Fiers, "Secondary Structure Of mRNA And Efficiency Of Translation Initiation", *Gene*, 9, pp. 1–12 (1980)].

Further increases in the cellular yield of the lipocortin-like polypeptides of this invention may be achieved by increasing the number of genes that can be utilized in the cell. This may be achieved by insertion of the lipocortin gene (with or without its transcription and translation control elements) into a higher copy number plasmid or into a temperature-controlled copy number plasmid (i.e., a plasmid which carries a mutation such that the copy number of the plasmid increases after shifting the temperature [B. Uhlin et al., "Plasmids With Temperature-Dependent Copy Number For Amplification Of Cloned Genes And Their Products", *Gene.* 6, pp. 91–106 (1979)].

Alternatively, an increase in gene dosage can be achieved, for example, by insertion of recombinant DNA molecules, engineered in the manner described above, into the temperate bacteriophage λ, most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", *Mol. Gen. Genet.*, 150, pp. 53–61 (1977), and N. E. Murray et al., "Molecular Cloning Of The DNA Ligase Gene From Bacteriophage T4", *J. Mol. Biol.*, 132, pp. 493–505 (1979)), and the recombinant DNA molecule produced by incubation with DNA ligase. The desired recombinant phage is then selected and used to lysogenize a host strain of *E.coli*.

Therefore, it should be understood that the lipocortin-like polypeptide coding sequences of this invention may be removed from the disclosed vectors and inserted into other expression vectors, as previously described (supra) and these vectors employed in various hosts, as previously described (supra) to improve the production of the human lipocortin-like polypeptides of this invention.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. An essentially pure lipocortin III selected from the group consisting of the amino acid sequences:

(a) MetAlaSerIleTrpValGlyHisArgGlyThrValArgAsp TyrProAspPheSerProSerValAspAla- GluAlaIleGlnLysAlaIleArgGlyIleGly ThrAsp- GluLysMetLeuIleSerIleLeuThrGluArgSerAs- nAlaGlnArgGlnLeuIle ValLysGluTyrGl- nAlaAlaTyrGlyLysGluLeuLysAspAspLeuLys- GlyAspLeuSer GlyHisPheGluHisLeuMet- ValAlaLeuValThrProProAlaValPheAs- pAlaLysGln LeuLysLysSerMetLysGlyAlaGly- ThrAsnGluAspAlaLeuIleGluIleLeuThrThr ArgThrSerArgGlnMetLysAspIleSerGlnAlaTyr- TyrThrValTyrLysLysSerLeu GlyAspAspIleSer- SerGluThrSerGlyAspPheArgLysAlaLeuLeuTh- rLeuAlaAsp GlyArgArgAspGluSerLeuLys- ValAspGluHisLeuAlaLysGlnAspAlaGlnIleLeu TyrLysAlaGlyGluAsnArgTrpGlyThrAspGluAs- pLysPheThrGluIleLeuCysLeu ArgSerPheProGl- nLeuLysLeuThrPheAspGluTyrArgAsnIleSerGl- nLysAspIle ValAspSerIleLysGlyGluLeuSer- GlyHisPheGluAspLeuLeuLeuAlaIleValAsn Cys- ValArgAsnThrProAlaPheLeuAlaGluAr- gLeuHisArgAlaLeuLysGlyIleGly ThrAspGlu- PheThrLeuAsnArgIleMetValSerArgSer- GluIleAspLeuLeuAspIle ArgThrGluPheLysLy- sHisTryGlyTyrSerLeuTyrSerAlaIleLys- SerAspThrSer GlyAspTyrGluIleTh- rLeuLeuLysIleCysGlyGlyAspAsp or, (b) AlaSerIleTrpValGlyHisArgGlyThrValArgAsp- Tyr ProAspPheSerProSerValAspAla- GluAlaIleGlnLysAlaIleArgGlyIleGlyThr Asp- GluLysMetLeuIleSerIleLeuThrGluArgSerAs- nAlaGlnArgGlnLeuIleVal LysGluTyrGl- nAlaAlaTyrGlyLysGluLeuLysAspAspLeuLys- GlyAspLeuSerGly HisPheGluHisLeuMet- ValAlaLeuValThrProProAlaValPheAs- pAlaLysGlnLeu LysLysSerMetLysGlyAlaGly- ThrAsnGluAspAlaLeuIleGluIleLeuThrThrArg ThrSerArgGlnMetLysAspIleSerGlnAlaTyr- TyrThrValTyrLysLysSerLeuGly AspAspIleSer- SerGluThrSerGlyAspPheArgLysAlaLeuLeuTh- rLeuAlaAspGly ArgArgAspGluSerLeuLys- ValAspGluHisLeuAlaLysGlnAspAlaGl- nIleLeuTyr LysAlaGlyGluAsnArgTrpGly- ThrAspGluAspLysPheThrGluIleLeuCysLeuArg SerPheProGlnLeuLysLeuThrPheAspGluTyrAr- gAsnIleSerGlnLysAspIleVal AspSerIleLysGly- GluLeuSerGlyHisPheGluAspLeuLeuLeuAlaIle- ValAsnCys ValArgAsnThrProAlaPheLeuAla- GluArgLeuHisArgAlaLeuLysGlyIleGlyThr Asp- GluPheThrLeuAsnArgIleMetValSerArgSer- GluIleAspLeuLeuAspIleArg ThrGluPheLysLy- sHisTryGlyTyrSerLeuTyrSerAlaIleLys- SerAspThrSerGly AspTyrGluIleTh- rLeuLeuLysIleCysGlyGlyAspAsp, from amino to carboxy terminal amino acids.

2. An essentially pure lipocortin III produced by a unicellular host transformed with a DNA molecule comprising a DNA insert selected from the group consisting of:

(a) a cDNA insert having the sequence GAATTC-CGATTAGTGTGATCTCAGCTCAAGG-CAAAGGTGGGATATCATGGCATC-TATCTGGGTT GGACACCGAGGAACAG-TAAGAGATTATCCAGACTTTAGCCCAT-CAGTGGATGCTGAAGCTATTC AGAAAG-CAATCAGAGGAATTGGAACTGAT-GAGAAAATGCTCATCAGCATTCTGACT-GAGAGGTC AAATGCACAGCGGCAGCT-GATTGTTAAGGAATATCAAGCAG-CATATGGAAAGGAGCTGAAAGAT GACTTGAAGGGTGATCTCTCTGG-CCACTTTGAGCATCTCATGGTGGCC-CTAGTGACTCCACCAG CAGTCTTT-GATGCAAAGCAGCTAAAGAAATCCAT-GAAGGGCGCGGGAACAAAC-GAAGATGCCTT GATTGAAATCTTAAC-TACCAGGACAAGCAGGCAAATGAAG-GATATCTCTCAAGCCTATTATACA GTATACAAGAAGAGTCTTGGAGAT-GACATTAGTTCCGAAACATCTGGT-GACTTCCGGAAAGCTC TGTTGACTTTG-GCAGATGGCAGAAGAGATGAAAGTCT-GAAAGTGGATGAGCATCTGGCCAAACA AGATGCCCAGATTCT-CTATAAAGCTGGTGAGAACAGATGGG-GCACGGATGAAGACAAATTCACT GA-GATCCTGTGTTTAAGGAGCTTTCCT-CAATTAAAACTAACATTTGAT-GAATACAGAAATATCA GCCAAAAG-GACATTGTGGACAGCATAAAAG-GAGAATTATCTGGGCATTTTGAAGACT-TACTGTT GGCCATAGTTAATTGTGT-GAGGAACACGCCGGCCTTTTTAGC- CGAAAGACTGCATCGAGCCTTG AAGGGTATTGGAACTGATGAGTTTACTCTGAACCGAATAATGGTGTCCAGATCAGAAATTGACC TTTTGGACATTCGAACAGAGTTCAAGAAGCATTATGGCTATTCCCTATATTCAGCAATTAAATCGGATACTTCTGGAGACTATGAAATCACACTCTTAAAAATCTGTGGTGGAGATGACTGAACCAAG AAGATAATCTCCAAAGGTCCACGATGGGCTTTCCCAACAGCTCCACCTTACTTCTTCTCATACT ATTTAAGAGAACAAGCAAATATAAACAGCAACTTGTGTTCCTAACAGGAATTTTCATTGTTCTA TAACAACAACAACAAAAGCGATTATTATTTTAGAGCATCTCATTTATAATGTAGCAGCTCATAA ATGAAATTGAAAATGGTATTAAAGATCTGCAACTACTATCCAACTTATATTTCTGCTTTCAAAG TTAAGAATCTTTATAGTTCTACTCCATTAAATATAAAGCAAGATAATAAAACGGAATTC, (b) a cDNA insert having the sequence ATGGCATCTATCTGGGTTGGACACCGAGGAACAGTAAGAGATTATCCAGACTTTAGCCCATCAG TGGATGCTGAAGCTATTCAGAAAGCAATCAGAGGAATTGGAACTGATGAGAAATGCTCATCAGCATTCTGACTGAGAGGTCAAATGCACAGCGGCAGCTGATTGTTAAGGAATATCAAGCAGCATAT GGAAAGGAGCTGAAAGATGACTTGAAGGGTGATCTCTGGCCACTTTGAGCATCTCATGGTGG CCCTAGTGACTCCACCAGCAGTCTTTGATGCAAAGCAGCTAAAGAAATCCATGAAGGGCGCGGGAACAAACGAAGATGCCTTGATTGAAATCTTAACTACCAGGACAAGCAGGCAAATGAAGGATATC TCTCAAGCCTATTATACAGTATACAAGAAGAGTCTTGGAGATGACATTAGTTCCGAAACATCTG GTGACTTCCGGAAAGCTCTGTTGACTTTGGCAGATGGCAGAAGAGATGAAAGTCTGAAAGTGGA TGAGCATCTGGCCAAACAAGATGCCCAGATTCTCTATAAAGCTGGTGAGAACAGATGGGGCACG . GATGAAGACAAATTCACTGAGATCCTGTGTTTAAGGAGCTTTCCTCAATTAAAACTAACATTTG ATGAATACAGAAATATCAGCCAAAAGGACATTGTGGACAGCATAAAAGGAGAATTATCTGGGCA TTTTGAAGACTTACTGTTGGCCATAGTTAATTGTGTGAGGAACACGCCGGCCTTTTTAGCCGAA AGACTGCATCGAGCCTTGAAGGGTATTGGAACTGATGAGTTTACTCTGAACCGAATAATGGTGT CCAGATCAGAAATTGACCTTTTGGACATTCGAACAGAGTTCAAGAAGCATTATGGCTATTCCCT ATATTCAGCAATTAAATCGGATACTTCTGGAGACTATGAAATCACACTCTTAAAAATCTGTGGT GGAGATGAC, (c) a DNA insert that hybridizes with a DNA insert of (a) or (b) above, in 5X SSC at 50° C., and that encodes a lipocortin III, or (d) a DNA insert with a sequence that is degenerate as a result of the genetic code as to the sequence of an insert of (a) or (b) above and that encodes a lipocortin III.

3. An essentially pure lipocortin III produced by a unicellular host transformed with a DNA molecule comprising a DNA insert selected from the group consisting of:

(a) the cDNA insert of lambda HLipo III-5, (b) a DNA insert that hybridizes to a DNA insert of (a) above, in 5X SSC at 50° C., and that encodes a lipocortin III, or (c) a DNA insert with a sequence that is degenerate as a result of the genetic code as to the sequence of the DNA insert of (a) above and that encodes a lipocortin III.

4. A pharmaceutically acceptable composition useful in the treatment of disorders involving inflammatory processes which comprises a pharmaceutically effective amount of at least one polypeptide according to any of claims 1, 2, or 3 and a pharmaceutically acceptable carrier.

5. A method for treating disorders involving inflammatory processes which comprises administering a pharmaceutically effective amount of a composition according to claim 4.

* * * * *